(12) United States Patent
Simeonov et al.

(10) Patent No.: US 11,934,923 B1
(45) Date of Patent: Mar. 19, 2024

(54) PREDICTIVE OUTPUTS IN THE PRESENCE OF ENTITY-DEPENDENT CLASSES

(71) Applicant: Swoop Inc., Cambridge, MA (US)

(72) Inventors: Simeon Simeonov, Lincoln, MA (US); Edward Zahrebelski, Dorchester, MA (US)

(73) Assignee: Swoop Inc., Cambridge, MA (US)

( * ) Notice: Subject to any disclaimer, the term of this patent is extended or adjusted under 35 U.S.C. 154(b) by 0 days.

(21) Appl. No.: 17/399,699

(22) Filed: Aug. 11, 2021

Related U.S. Application Data

(60) Provisional application No. 63/064,099, filed on Aug. 11, 2020.

(51) Int. Cl.
*G06N 20/00* (2019.01)
*G06F 18/241* (2023.01)
*G16H 10/00* (2018.01)

(52) U.S. Cl.
CPC .......... *G06N 20/00* (2019.01); *G06F 18/241* (2023.01); *G16H 10/00* (2018.01)

(58) Field of Classification Search
CPC .. G06K 9/6228; G06K 9/6218; G06K 9/6256; G06K 9/6262; G06K 9/6268; G06K 9/6271; G06N 3/084; G06N 3/0454; G06N 3/08; G06V 10/82
See application file for complete search history.

(56) References Cited

U.S. PATENT DOCUMENTS

| 11,244,029 B1* | 2/2022 | Benner ................. G16H 10/60 |
| 2015/0302163 A1* | 10/2015 | Das .......................... G06N 3/02 705/2 |
| 2018/0314947 A1* | 11/2018 | Morris, II ............. G06N 20/00 |
| 2018/0329951 A1* | 11/2018 | Yu .......................... G06N 20/00 |
| 2022/0036605 A1* | 2/2022 | Riddell ................ A61B 6/4208 |

* cited by examiner

*Primary Examiner* — John W Lee
(74) *Attorney, Agent, or Firm* — Goodwin Procter LLP

(57) ABSTRACT

The quality of predictive model outputs is improved by improving input data in the cases where entities in the input data are associated with one or more classes, computed at least in part from one or more subsets of the input data. Class association function characteristic data is derived from information describing a class association function that generates input data from source data. The class association function characteristic data comprises inferences relating to operation of the class association function that are not derivable solely from the input data. The input data is transformed into improved input data using a constructed class-specific transformation function and the class association function characteristic data.

30 Claims, 5 Drawing Sheets

PREDICTIVE OUTPUTS IN THE PRESENCE OF ENTITY-DEPENDENT CLASSES

CROSS-REFERENCE TO RELATED APPLICATION

This application claims priority to and the benefit of U.S. Provisional Patent Application No. 63/064,099, filed on Aug. 11, 2020, the entirety of which is incorporated by reference herein.

FIELD OF THE INVENTION

This disclosure relates generally to machine learning (ML) and artificial intelligence (AI) and, more specifically, to methods and systems for improving predictive outputs of ML/AI models by improving input data using entity-class association.

BACKGROUND

With existing techniques, data science algorithm input data is treated as invariant to downstream data science processing (DDSP) of the input data. Traditionally, DDSP focuses on sampling and featurization to create the inputs to data science algorithms, such as but not limited to, training and testing data for predictive models. In particular, existing techniques treat class association functions as largely independent of DDSP where their influence on DDSP is entirely determined by the class information associated with entities in the input data. More specifically, information concerning the construction of a class association function or its properties affect DDSP in these techniques.

BRIEF SUMMARY

In one aspect, a method of improving quality of predictive model outputs comprises the steps of receiving information describing a class association function that generates input data from source data, wherein the source data comprises a plurality of entities of one or more entity types, and wherein the input data comprises a combination of the source data with class information such that entities in the input data are associated with one or more classes; deriving, from the information describing the class association function, class association function characteristic data comprising inferences relating to operation of the class association function that are not derivable solely from the input data; constructing a class-specific transformation function that transforms the input data into improved input data; and transforming, using a computer processor, the input data into the improved input data using the class-specific transformation function and the class association function characteristic data. In another aspect, a method of improving quality of predictive model outputs comprises the steps of receiving class association function characteristic data derived from information describing a class association function that generates input data from source data, wherein the source data comprises a plurality of entities of one or more entity types, wherein the input data comprises a combination of the source data with class information such that entities in the input data are associated with one or more classes, and wherein the class association function characteristic data comprises inferences relating to operation of the class association function that are not derivable solely from the input data; constructing a class-specific transformation function that transforms the input data into improved input data; and transforming, using a computer processor, the input data into the improved input data using the class-specific transformation function and the class association function characteristic data. Other aspects of the foregoing include corresponding systems and computer-executable instructions stored on non-transitory storage media.

In one implementation, the method further comprises generating, using the computer processor, the input data by providing the source data as input to the class association function and receiving the input data as output from the class association function. The source data can comprise data stored in computer memory, a database, data warehouse, data lake, data lakehouse, file system or object store. The information describing the class association function can comprise a class association function that is directly introspectable. The information describing the class association function can comprise a class association function that is not directly introspectable. The information describing the class association function can be received from an external source.

In another implementation, receiving the information describing the class association function comprises generating the information describing the class association function by approximating at least a portion of the class association function using information inferred from the source data and the class information. The deriving can comprise one or more of: (i) extracting entity-related information from the class association function; (ii) applying the class association to one or more subsets of the input data to identify entity-level attributes; and (iii) analyzing the information describing the class association function to determine an approximate implementation of the class association function.

In another implementation, the information describing the class association function is incorporated into the class-specific transformation function, such that the class-specific transformation function generates the input data from the source data. The information describing the class association function information can be either incorporated into the class-specific transformation function or used as in input to the class-specific transformation function.

In another implementation, the method further comprises providing the improved input data as input to a predictive model and predicting, using the predictive model, whether a particular entity will be assigned to a particular class. The improved input data, when used as input to a predictive model, can result in the predictive model providing output of greater predictive accuracy compared to use of the input data as input to the predictive model.

In another aspect, a method of improving quality of predictive model outputs for a healthcare system comprises the steps of receiving information describing a class association function that generates input data from source data, wherein the source data comprises healthcare information associated with a plurality of participants associated with a healthcare system, and wherein the input data comprises a combination of the source data with class information such that participants associated with the healthcare system in the input data are associated with one or more classes; deriving, from the information describing the class association function, class association function characteristic data comprising inferences relating to operation of the class association function that are not derivable solely from the input data; constructing a class-specific transformation function that transforms the input data into improved input data; transforming, using a computer processor, the input data into the improved input data using the class-specific transformation function and the class association function characteristic data; and providing the improved input data as input to a predictive model and predicting, using the predictive model, whether a particular participant associated with the healthcare system will satisfy a healthcare-related condition. Other aspects of the foregoing include corresponding systems and computer-executable instructions stored on non-transitory storage media.

In one implementation, the predicting comprises predicting, using the predictive model, whether the particular participant associated with the healthcare system will satisfy a predicate over data associated with the particular participant. The predicate can comprise a patient receiving a diagnosis, a patient receiving a procedure, a patient receiving a treatment, a healthcare professional making a diagnosis, a healthcare professional performing a procedure, a healthcare professional prescribing a treatment, a payer making a payment, a payer rejecting a claim, or any combination of the foregoing.

In another implementation, deriving the class association function characteristic data comprises determining that entities are assigned to the one or more classes based on a first date associated with a first predicate over data associated with the entities. Deriving the class association function characteristic data can comprise determining that entities are assigned to the one or more classes based on a relation of (i) the first date associated with the first predicate to (ii) a second date associated with a second predicate over the data associated with the entities. Transforming the input data into the improved input data can comprise filtering the input data to remove information associated with dates (i) temporally following an earliest date of the second predicate and/or (ii) temporally preceding an earliest date of the second predicate.

In another implementation, deriving the class association function characteristic data comprises determining that entities are assigned to the one or more classes based on an occurrence of a healthcare-related event comprising starting a therapy, receiving a treatment, receiving a procedure, or receiving a diagnosis. Transforming the input data into the improved input data can comprise filtering the input data to remove information associated with dates having a particular temporal relationship to a time or date associated with the healthcare-related event. The particular temporal relationship can comprise an earlier time or data, a later time or date, or a same time or date. The participants associated with the healthcare system can comprise patients, healthcare providers, healthcare-related organizations, and/or payers.

The details of one or more implementations of the subject matter described in the present specification are set forth in the accompanying drawings and the description below. Other features, aspects, and advantages of the subject matter will become apparent from the description, the drawings, and the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the implementations. In the following description, various implementations are described with reference to the following drawings.

DESCRIPTION OF THE INVENTION

Figure 1:
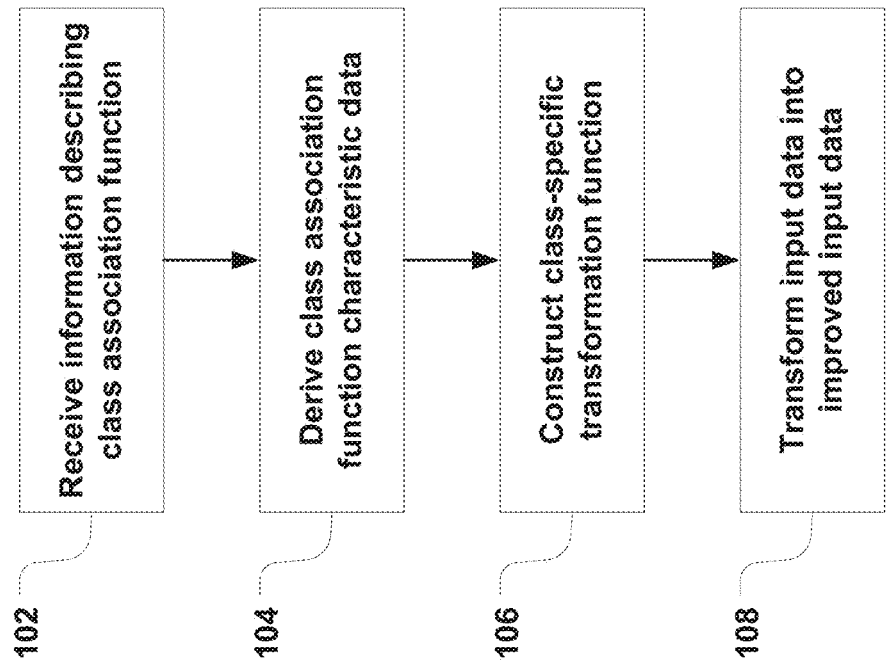
FIG. 1 depicts a method of improving the quality of predictive model outputs, according to an implementation.

In the domain of data science, the quality and richness of input data plays a key role in the quality of ML/AI outputs. The present disclosure teaches methods for improving predictive outputs by improving input data in the cases where entities in the input data are associated with one or more classes, computed at least in part from one or more subsets of the input data. In addition to providing the aforementioned improvements to the ML/AI technological fields, the disclosed techniques improve the performance and efficiency of computers used for ML/AI modelling by reducing, refining and otherwise transforming model input data so that, in some instances, reduced processing time and effort is necessary. Advantageously, this technique for improving processing performance also results in more accurate, higher quality predictive output data from ML/AI models.

Without loss of generality, the following terms used herein are defined as follows:

(1) Source data (SD) is data that can be represented in a format useful for performing the operations described herein. In one implementation, source data is represented in a familiar single table-like manner as rows and columns, where columns can have arbitrary complexity, to avoid the need to consider multi-table operations such as joins and alternative data representations that carry no additional representative power. State of the art enhancements to source data, e.g., via joins in traditional table-based data parlance or via computed fields, can be considered to have already been made.

(2) Entities are the things for which predictions are computed, as further described herein. Source data can have entities from one or more entity types. Generalizations to the powerset of all entity types are trivial as each subset of the set of entity types can be considered a new entity type in its own right. Source data can be partitionable into row subsets about each entity, which need not be mutually exclusive.

(3) Classes are categorical attributes of entities. A single class is typically associated with a single entity type. Class-entity type association need not be mutually exclusive. A class-value pair is the combination of a class with a specific value of its categorical attribute. In some implementations, at least one class is associated with an entity based at least in part on the rows associated with the entity. Such classes are termed "entity-derived classes."

(4) Input data (ID) is the combination of source data with class information (CI). Class information can include the class attributes as well as related state of the art data enhancements. As consistent with the state of the art, these data enhancements are individual-entity-independent but may be dependent on ID as a whole. This distinction between SD and ID acknowledges the fact that data about entity-derived classes came into existence after source data as it depends on it. In function terms, ID=CAF(SD, . . . ), where CAF is the class association function.

(5) Attributes, logically speaking, are functions that compute values based on rows and columns in data. For purposes of simplification, attributes can be considered as materialized as individual columns whose values for each row are the same as the value of the attribute. When an attribute is computed from a group of rows, e.g., those associated with a specific entity or an entity type, the attribute may have the same value for each row in the group or a value otherwise computed from the group, e.g., similar to the way window functions operate in SQL.

With the assumption of state of the art data enhancements already performed, in the state of the art, ID is treated as invariant to DDSP of ID. Traditionally, DDSP focuses on sampling and featurization to create the inputs to data science algorithms, such as but not limited to, training and testing data for predictive models. In particular, the state of the art treats CAF as largely independent of DDSP where its influence on DDSP is entirely determined by the class information associated with entities in ID. More specifically, information concerning the construction of the CAF or properties of the CAF affect DDSP in the state of the art.

The present disclosure improves on the state of the art by describing a general-purpose method for improving the richness and/or quality of ID prior to traditional DDSP by using externally provided or internally inferred information about the CAF and transforming ID into improved input data (IID). For example, this method allows for, among other things: (1) the association of valuable additional attributes with entities; (2) the removal of subsets of ID that may negatively impact data science computations; (3) other transformations; and (4) novel model selection and ensembling techniques based on the net new data in IID.

FIG. 1 depicts an example method of improving the quality of predictive model in accordance with the techniques described herein. In Step 102, information is received describing a class association function that generates input data from source data. The source data includes entities that have an entity type, and the input data combines the source data with class information so that entities in the input data are associated with one or more classes. In Step 104, class association function characteristic data is derived from the information describing the class association function. The class association function characteristic data includes inferences relating to the operation of the class association function that are not derivable solely from the input data. In Step 106, a class-specific transformation function is constructed, which transforms the input data into improved input data. In Step 108, using the class-specific transformation function and the class association function characteristic data, the input data is transformed into the improved input data. The foregoing method is described in further detail below.

Without loss of generality, the rest of the description will focus on a single entity type (E) and a single class-value pair of a single entity-derived class about this entity type, henceforth called C. Any combination of classes and their class-value pairs may be modelled as a set of 1-hot-encoded classes, one per class-value pair. The method is trivially generalizable to multiple entity types via a combinator function that brings together the output of the method described in this disclosure for each entity type from ID into IID. In some implementations such combinators may be a union, a distinct union, a SQL query, or an operation represented using a sequence of map-reduce steps. To simplify the description further, the focus will be on the subset of rows of E that are associated with C (relevant data: RD). Rows not associated with C, as well as those not associated with E, are transformed in the creation of IID, before the combinator, in a structurally similar manner, but with "empty" information. For example, if the RD portion of IID introduces a new column, the same column would be present in rows of IID not associated with RD, but with a default value, such as NULL. Similarly, in an implementation where the RD portion of IID adds or removes rows from a subset of RD, the transformation would function as a no-op transform on rows of IID not associated with RD where no rows outside of RD would be added or removed.

CAF associates at least one entity-derived class with E in SD. Therefore, the information describing CAF (e.g., definition, specification, function, source/binary code, implementation, representation, etc.) includes information related to the rows and/or columns of E in SD. The system can directly receive this information describing the CAF from an external source, or it can infer the information internally using SD and CI to approximate all of or part of CAF. Some of this information from CAF can be "extractable" as data (CAFD), also referred to herein as class association function characteristic data. In addition, access to CAF itself can in some circumstances be available, i.e., the ability to assign a class to a subset of rows with the entity type from E by "applying" CAF, or some appropriate representation thereof. It is then possible to construct a new class-specific transformation function (CSTF) that transforms ID into IID as follows:

$$IID=CSTF(ID,CAFD,CAF)$$

In some implementations, all of or part of CAF can be approximated (CAFa). When such a part of CAF is approximated (which can also be the whole of CAF), a subset of the observed domain of CAF in SD is used to infer an approximate mapping to a subset of the range of CAF. In some implementations, any approximation step takes place during data processing for the benefit of DDSP where the objective of the approximation step is independent of the objectives of DDSP and separate from any downstream ML/AI modeling pipeline trained and executed on IID. CAFa can affect the construction and/or behavior of CSTF by affecting CAFD directly, by being added as an input in the IID formula above, or even by replacing CAF. This observation generalizes trivially to more than one CAFa.

Embodiments that approximate CAF can use ML/AI methods to learn CAFa as follows:
1. Identify number of training rows, NT, number of validation rows, Nv, and performance threshold, X, with NT, Nv, and X greater than or equal to 0.
2. Sample NT rows of ID as training data and sample a subset of same as validation data.
3. Fit classifier to the training data to get C*.
4. If performance of C* on validation data is better than X, return C*.

For system implementations utilizing ML/AI techniques to learn CAFa, overfitting can optionally be employed. The states where overfitting provides benefit may include those where the entire potential domain of CAFa is known a priori and accessible or observable. To learn an overfit representation, the system can over specify model parameter space, allow unbounded model complexity, or withhold little to no data for validating model generalizability. One such algorithm using a decision tree for constructing an overfit CAFa is as follows, though any sufficiently flexible classifier can be used:

1. Identify minimum threshold accuracy, X, that corresponds to adequately learning to approximate CAF with X between 0 and 100%.
2. Sample all rows of ID as training data.
3. Fit various decision trees with no (or a sufficiently large) depth restrictions to the training data.
4. Return (the smallest) decision tree that achieves accuracy at least X on the training data.

Another example of an algorithm for constructing an overfit CAFa is as follows:
1. Identify minimum threshold accuracy, X, that corresponds to system adequately learning to approximate the true CAF and create IID with X between 0 and 100%.
2. Sample all rows of SD and corresponding CI as training data.
3. Fit various flexible classifiers $\{C_i\}$, i=1 to m, with no complexity restrictions.
4. Return the least complex classifier C* that achieves accuracy at least X on the training data.

Other implementations can receive some external yet incomplete information about CAF and seek to enhance the information by learning a richer representation of CAF using some knowledge of CAF, observing the action of CAF on rows in SD, or learning a CAFa. In these implementations, general knowledge about the type of data in SD used to assign classes to entities can inform the training and model search space for learning CAFa. For example, if a system implementing the described techniques receives information about the type of data that determines class assignment, these implementations can employ methods such as rule induction, tree-based models, bump hunting, or other data mining and ML methods to learn CAFa that improve the system's knowledge of CAF. The system can then leverage this enhanced information to produce CAFD that improves the precision and potency of the CSTF.

When implementations approximate CAFa via ML techniques, if the functional form of CAFa is interpretable, data concerning CAFa can be directly extracted to produce CAFD. If CAFa is learned through black box methods such as a Deep Neural Network, the system can leverage black box model interpretability and explainability techniques to produce CAFD or even construct another CAFa.

In some embodiments, CAF can be implicitly designed into CSTF, and both applied in a single system step, such that ID is effectively IID: ID=CSTF(SD, CAFD, CAF).

In various implementations CSTF can be represented as data transformation plans such as SQL operations, map-reduce operations, Apache Spark transformations, etc. These common implementations do not preclude other implementations, including implicit ones where DDSP operates on ID directly but DDSP behavior is modified based on knowledge of the behavior of CSTF, e.g., by hard-coding or parameterizing a featurization strategy of ID in a manner that generates output substantially equivalent to DDSP operating on the new data added to IID.

Note that the creation and application of more than one CSTF and downstream processing of several IIDs is generalizable to a single CSTF that adds attributes (columns) to IID such that the attributes allow for differentiating between the rows of each IID that would have been created by the separate CSTFs.

CAF, logically speaking, produces output at the entity level, but that does not mean the output is entirely independent of other entities' data. In implementations where CAF output is solely dependent on a single entity's rows, CSTF can benefit from partitioning, distribution and/or parallelization of processing at the entity level. In implementations where the maximum number of rows associated with a single entity allows the necessary portion of a single entity's data to be represented in the random access memory (RAM) of a single processing unit, it may be desirable to organize data representation and I/O such that the whole or part of CSTF operates on all the data for a single entity in a single processing unit's RAM.

In implementations in the domain of automated machine learning (AutoML), CSTF can operate in a manner that is somewhat independent of the objective(s) ID is intended for, typically aiming to generate one or more additional attributes of ID that downstream data science processes can flexibly use in filtering, (over/under-)sampling and featurization strategies. By introducing net new information in IID, not included in state-of-the-art ID generation, this method indirectly improves AutoML state of the art, by expanding into a new domain of AutoML for data with entity-dependent classes.

In some implementations, it is preferable to treat IID as multiple "versions" of ID, each undergoing DDSP substantially similar to what ID would have undergone in the absence of this disclosure. This is particularly beneficial in situations where it is impractical or expensive to make changes to DDSP based on the data improvements in IID. These multiple versions can be processed in parallel where desired. The output of traditional DDSP intended for ID across versions can then be reduced to produce the output of DDSP in the presence of the describes techniques. In one implementation, a best output for a single version can be selected. In another implementation, a subset of outputs can be selected to build an ensemble output. In yet another implementation, various measures about DDSP may can computed to aid in determining the quality of the data science process. In this manner, this disclosure improves the state of the art in model selection and validation, as well as ensemble learning.

CAFD does not necessarily need to be an argument to CSTF: any part of CAFD can be "designed into" the implementation of CSTF, just as it was in CAF. In one implementation, where CSTF is represented as a SQL query, part of CAFD can be a subexpression in the WHERE clause of such a query. By the same argument, CAF may not need to be an argument to CSTF as it may be designed into CSTF's implementation.

In some implementations, CAFD may be derived from the application of CAF on other data (not the source data) or functions similar in some way to CAF on the source data or other data.

Aspects of CAF can be analyzable by algorithms that automatically construct the whole or part of CAFD and, optionally, CSTF. In some implementations, CAF may have a representation as a graph, e.g., an abstract syntax tree (AST), or a data transformation plan, or an object instance graph in the memory of a virtual machine. Algorithm(s) can operate on these representations to enhance ID with additional columns based on CAFD discovered during graph processing. For example, the graph can include predicate expressions that refer to column names and values from SD.

The absence of certain graph nodes, edges or higher-level structures can also provide information about CAF. For example, if CAF is represented as a data transformation plan over SD, and analysis determines that (a) CAF does not refer to external data with entity IDs and (b) that the transformation does not group or otherwise aggregate SD rows, it can be inferred that CAF assigns C based on a row-level predicate. That predicate can be extracted from CAF's representation and used directly in CSTF to replicate CAF's behavior.

In some implementations, CAF can take the form of a data operation, such as SQL-like join of a class table (CT) with entity IDs and class information to the source data based on entity IDs. In such implementations, CAFD may be discoverable in the implementation of the operation that generated CT, e.g., the SQL query that determined the composition of its rows.

CAF need not be fully defined/described for CAFD to be derived. As an example, if may be known that CAF assigns a certain class when condition 1 is true and some other condition(s) are true. If only condition 1 is introspectable, or information about it is available in some other way, that still could result in valuable CAFD. If condition 1 is "gender is male", it is known that CAF will never assign the class when gender is not male. Note that, in the state of the art, one could observe that, in the data, the class is only assigned to males but, without the additional information about CAF, one cannot reason with certainly whether this observation is merely an accidental property of the data or true in general.

In an implementation where SD represents discrete events with some full or partial ordering, and where CAF assigns C based on the presence of at least one event matching a predicate that is discoverable by analyzing CAF's representation, CSTF can be constructed in part to assign attributes that indicate the ordered position of a row, or the information therein, relative to one or more rows that individually or together match the predicate, such ordered position being, for example, before, at, or after the first row, or attributes thereof that determine ordering, that contributed to the predicate being matched.

Independently of the mechanism for discovering that C is assigned on a row-by-row basis by CAF, that knowledge is useful for automatically generating attributes of IID at the entity level. In the case of discrete events with full or partial ordering, it allows for the efficient automatic construction of attributes such as minimum and maximum positions in the ordering (or their associated ordering attributes, such as, for example, a date or timestamp) via grouping-like or window-function-like processing of ID by entity.

In some implementations, CSTF may be created with a bias towards aiding specific downstream data science task(s). For example, in a classification scenario, where SD represents discrete events with some full or partial ordering, and where CAF assigns C based on the presence of at least one event matching a predicate, CSTF may be constructed in part to remove all rows at or after the first row matching the predicate. In an IID-as-multiple-ID-versions implementation, two versions of ID, one unchanged and one with the abovementioned rows removed can be created and the outputs of DDSP for each analyzed to determine the benefit of the row removal strategy.

Row-level attributes of ID added by parts of CSTF can be transformed into entity-level attributes, replicated by row for each entity, as needed, via an aggregation function operating on the rows for the entity.

CSTF can filter, (over/under-)sample and/or otherwise transform ID to create IID based on attributes derived at least in part from CAFD and/or applications of CAF, whether these attributes are included in IID or not.

In some implementations, CAF can be used directly to generate new attributes of ID. In these embodiments, the output of CAF can be used in lieu or in addition to an ability to "introspect" CAF to create CAFD. One such technique involves applying CAF to one or more subsets of an entity's (one that belongs to C) rows in ID to create entity-level attributes, as follows:

1. Identify one or more subsets of the rows such that the entity would be considered assigned to the class based on each of these subsets, without regard to any other rows.
2. Select or compute at least one attribute per subset, optionally, in the context of all data for the entity, the class, the entity type, and ID, or some subset thereof.
3. Reduce attributes across subsets so that they become attributes of the entity.
4. Replicate the attributes across all rows for the entity.
5. Transform the data based on the attributes.

In some implementations, the subsets in step (1) above are minimal subsets, i.e., ones where the entity is part of the class and removing any row from the subset would cause the entity to not be considered part of the class. The duality of applying CAF on subsets of an entity's rows vs. introspecting CAF to create CAFD is a powerful idea that increases the applicability and value of this invention across a broad range of situations. For example, consider a variation of the classification scenario described above, with the constraint that CAF's definition and implementation are completely opaque and, therefore, CAFD is the empty set. Here is how CAF can be applied using the algorithm described above to achieve the same result: remove all rows at or after the first row matching the (now completely opaque) predicate:

1. Identify the minimal subsets.
2. Select the first event ordering attribute(s) from the subset.
3. Reduce using a minimum, selecting the first event's ordering attribute(s) across all sub sets.
4. Replicate the attributes across all rows for the entity.
5. Remove the rows where a row's own ordering attribute(s) are at or after the first event's ordering attribute(s).

Some implementations may achieve the computation of specific attributes based on CAF in an optimized manner, without resorting to the general-purpose algorithm operating on subsets. For example, knowledge of the reduction function, e.g., min/max, can be used to reduce the number of CAF applications. In the above example, rather than generating first event attributes for all minimal subsets up front, before reducing, it may be beneficial to use a "rolling" minimum. It is not worth processing any subset where all events are later than the current minimum. In some cases, the following algorithm can provide near-optimal performance (pseudocode below is at the scope of a single entity from C):

1. i=0, events={ }
2. while CAF(events) does not associate events with C
   2.1. i=i+1
   2.2. Add the $i^{th}$ event (in order) to events
3. min=1
4. Remove $min^{th}$ event from events
5. while CAF(events) associates events with C
   5.1. min=min+1
   5.2. Remove $min^{th}$ event from events
6. Use the ordering attribute(s) of the $min^{th}$ event to transform the data (add the attribute, filter/change rows, etc.)

Example 1

Figure 2:
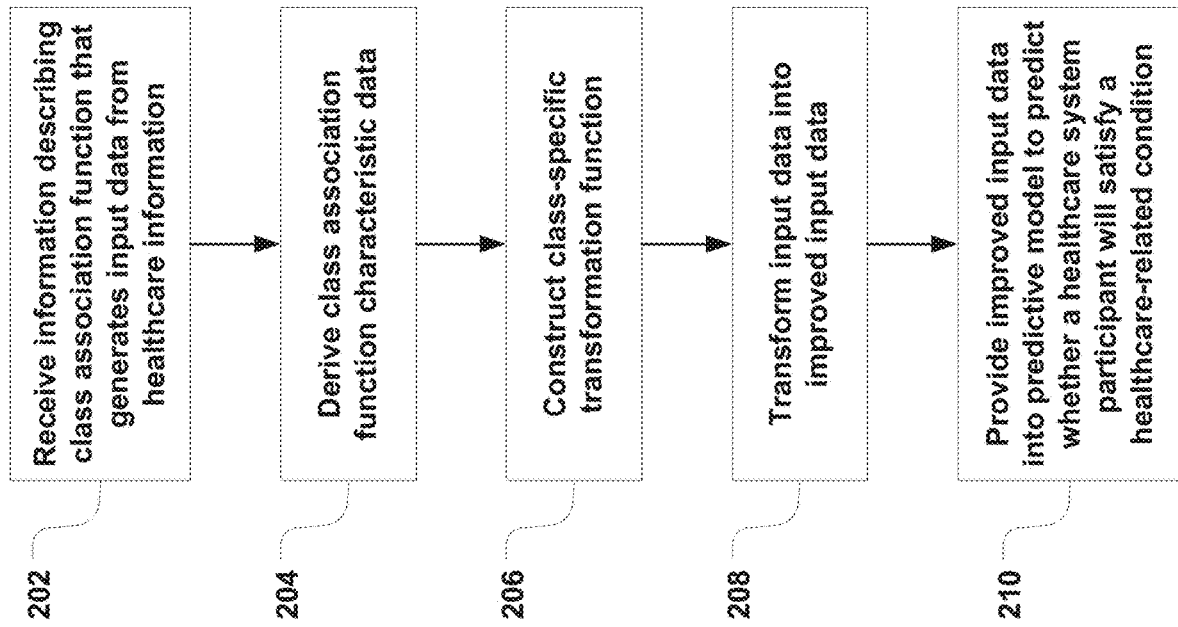
FIG. 2 depicts a method of improving the quality of predictive model outputs for a healthcare system, according to an implementation.

In one implementation, the above-described techniques can be used to improve the ability of a predictive model to predict whether a healthcare system participant will satisfy a healthcare-related condition. FIG. 2 depicts one implementation of a method of improving the quality of predictive model outputs for a healthcare system, in accordance with the techniques described herein. In Step 202, information describing a class association function that generates input data from source data is received. The source data includes healthcare information associated with participants in a healthcare system, and the input data combines the source data with class information such that participants in the healthcare system that are in the input data are associated with one or more classes. In Step 204, class association function characteristic data is derived from the information describing the class association function. The class association function characteristic data includes inferences relating to the operation of the class association function that are not derivable solely from the input data. In Step 206, a class-specific transformation function is constructed that transforms the input data into improved input data. In Step 208, the input data is transformed into the improved input data using the class-specific transformation function and the class association function characteristic data. In Step 210, the improved input data is provided as input to a predictive model, which is used to predict whether a particular participant associated with the healthcare system will satisfy a healthcare-related condition. One implementation of the foregoing method will now be described.

Consider the problem of predicting whether a patient satisfies a health requirement. The patient universe is divided into two classes: patients known to satisfy the requirement (positives) and patients not known to satisfy the requirement (unknowns). The rule for satisfying the requirement is receiving a medical procedure P within three months of receiving one of more medical diagnoses (D).

One way to approach the problem is to train a binary classifier against training data compiled from the positives and the unknowns. In the state of the art, some sampling will be performed to select patients from the positive and unknown classes, followed by the typical iterative ML process of experimenting with featurization, training and validation. However, the information captured in the class association function (receiving a medical procedure P within three months of receiving one or more medical diagnoses) would not be present in the data and, therefore, cannot be used to transform the data to improve prediction accuracy.

Before this process begins, this invention could be used as follows for the positive patient class, leaving the unknown class unchanged:
1. For each patient
   1.1. Identify all pairs of observations where a qualified diagnosis D is followed within 3 months by P.
   1.2. For each pair, select the date of the diagnosis.
   1.3. Reduce that to the minimum date across all pairs.
   1.4. Filter the patient's data to rows, assuming one diagnosis/procedure per row, earlier than the minimum date.
2. Union all patient data together to get the transformed positive class. (The unknown class remains unchanged in this example.)

Two simple approaches for achieving the above will now be described, specifically looking at CAF, the information extracted from it, and how input data ID may be transformed into improved input data IID.

First, the information extracted from CAF is that classes are assigned based on the relation of dates associated with P and D. In causal reasoning, it can be said that there is a causal relationship between the dates of P and D in a patient's medical history and the class, without necessarily knowing what the relationship is, or one can be more specific. In this case, it seems clear that the date of the first diagnosis is quite important as the patient is "on the path" to receive procedure P after one or more D is necessary, but one D alone is sufficient.

Second, this data can be materialized from CAF as CAFD by adding a column along the lines of date_of_first_D. In that case the filtering step is simply the equivalent of "where date<date_of_first_D". Note that date_of_first_D need not be materialized as a separate column of IID in memory, on disk, etc. It could be implicitly computed during a data transformation, achieving the same end result. If the data transformation language were SQL, the computation and transformation can use any number of techniques known to experts in the art: self joins, window functions, etc.

Example 1 Analysis

The rules that define classes carry data. In the example above, it is D and P and three months, etc. That data is exogenous to the source data and typically not "materialized" in the state of the art. Therefore, converting source data into featurized data cannot make decisions based on this exogenous data. While state of the art data processing may be class-specific, e.g., performing sampling at different rates per class, based on the number of entities per class, to balance class sizes, the scope of that processing is naturally limited to the available data, which excludes the medically-relevant data from class rules.

Example 2

This example extends the ideas presented in Example 1 for a different prediction task and displays the results of a real-world case study comparing this invention to the state of the art when evaluated on actual health data. Here, a healthcare ML system leveraged this invention to predict which patients were most likely to start a particular therapy (T) or receive diagnosis (D).

For this application, patient entities and their respective health data were considered together as source data. The predicate determining positive class membership functioned as the CAF, which assigned positive class membership to patient entities who had D or T in their health histories. The predicate returned 0/1 class membership information, CI, for each patient dependent on the health history. Those who satisfied the predicate received a label of 1, and those who did not received a label of 0. The system implementing the described method then column-appended patient-level class information output by CAF to patient records in the source data SD. The resulting combination of source data with entity information and CI yielded current state-of-the-art input data, ID, with entity driven classes determined by the predicate behind the CAF.

After saving ID, an implementation generated improved input data for downstream data science processing or DDSP. To do this, the system utilized the algorithm described below, which applied the CAF to all observations, emitted CAFD for each observation consisting of the earliest date the CAF predicate returned a positive value for that specific entity, and applied the CSTF to each enhanced observation to remove observations occurring after the minimum of the first occurrence of diagnosis D or start of therapy T for all positive patients. The resulting transformed data was IID.
1. Extract CAFD from CAF, obtaining D & T.
2. Implement CSTF as follows:
   2.1. For all rows with label value of 0, leave the rows unchanged.
   2.2. For all rows with label value of 1.
      2.2.1. Find the earliest date by patient of rows related to D or T.
      2.2.2. Remove rows happening after the date from 2.2.1.
3. Apply CSTF to ID to create IID.

To test the effectiveness of the described technique, we trained a model (M) with hyperparameter set (H) on all rows belonging to a randomly chosen sample of patient entities in IID where patients belonged to either the positive (CI=1) or unknown (CI=0) class in order to produce a function ($F_E$) that predicts whether a general patient will be a member of the positive class. For comparison, we examined performance on a random sample from the current state-of-the-art, ID, and trained M with H on exactly the same patient entities and all of their corresponding rows in ID to produce another function ($F_N$) that also predicts whether a general patient will be a member of the positive class. Finally, we evaluated both $F_E$ and $F_N$ on a holdout set (S) that contained patient data for patients that we knew were members of the positive class and patients that never became members of the positive class within a prespecified time window. For that reason, we consider them examples of true negatives since the patient data in the holdout set was pulled prior to knowing whether any patients in the holdout set were positive. Therefore, the trained models, $F_E$ and $F_N$, were unable to rely on the predicate for inference since the events had not yet occurred for any patients in the holdout set.

The terminology used herein as applied to the foregoing example is as follows:
  Entity: patient.
  Source Data: patient health records, one row per diagnosis/treatment/etc.
  CAF: return 1 if a patient's history contains diagnosis D or treatment T, 0 otherwise.
  CI: single patient class label, computed via CAF.
  ID: source data, with CI associated for each patient.
  CAFD: information related to determining whether a row of source data relates to D or T.
  CSTF: for patients where CAF is 1, remove all rows of data after the earliest date of D or T (from CAFD) in a patient's history.
  IID: the result of transforming ID with CSTF.
  DDSP: ML models trained on ID and IID with comparative evaluation and best model selection.

Example 2 Analysis

The effect of utilizing an end date filter is pronounced with $F_E$ performing significantly better than $F_N$ on the holdout set.

The confusion matrices below for $F_N$ and $F_E$ exhibit each model's performance on the holdout set. By utilizing the invention described herein, $F_E$ performs about 100 times better with respect to recall (true positives/total positives) without sacrificing virtually any precision.

Confusion Matrix for $F_N$ (without end date filter)

|  | Predicted Positive | Predicted Negative |
| --- | --- | --- |
| True Positive | 0.003 | 0.997 |
| True Negative | 0.0001 | 0.999 |

Confusion Matrix for $F_E$ (with end date filter)

|  | Predicted Positive | Predicted Negative |
| --- | --- | --- |
| True Positive | 0.39 | 0.61 |
| True Negative | 0.01 | 0.99 |

Figure 3A:
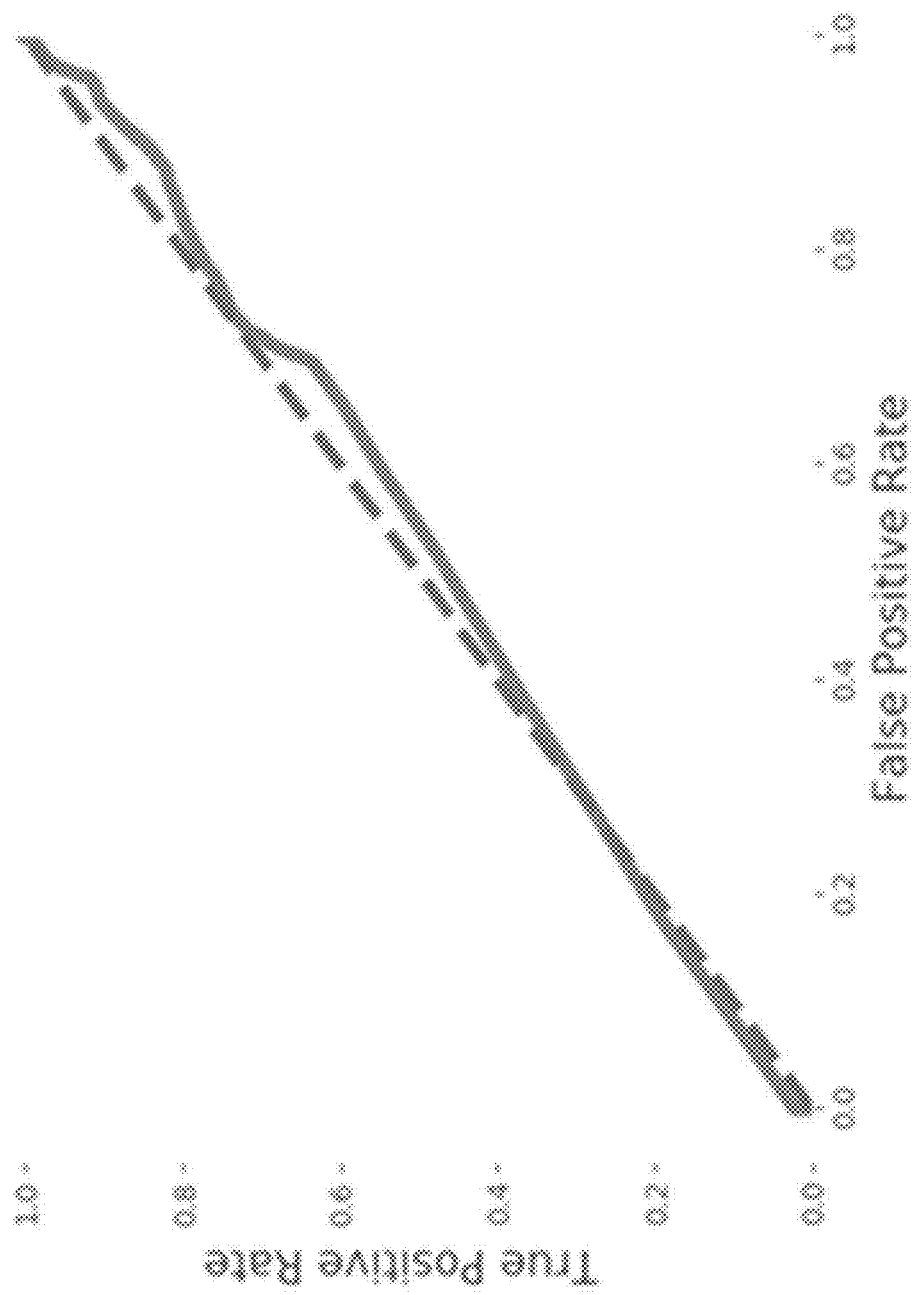
FIGS. 3A and 3B depict receiver operating characteristic curves associated with different models.
Figure 3B:
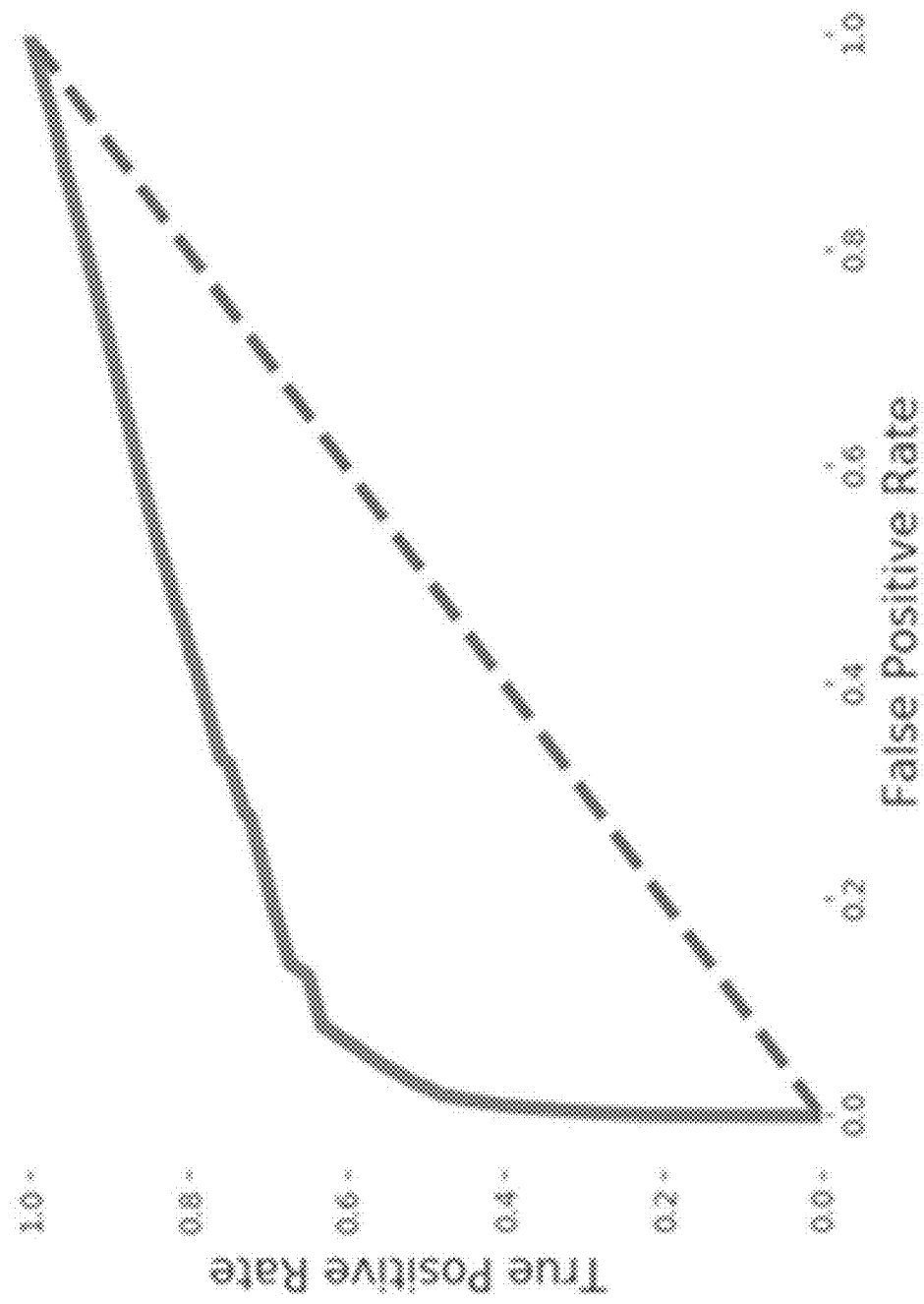

The corresponding receiver operating characteristic (ROC) curves for each model further illustrate the difference. FIG. 3A depicts the ROC curve for $F_N$ without the end date filter, and FIG. 3B depicts the ROC curve for $F_E$ with the end date filter. Just as with the confusion matrices, $F_N$ performs no better than random on unseen holdout data achieving an AUC of roughly 0.48. Meanwhile, $F_E$, the model trained with rows occurring after the end date removed performs quite well on unseen data achieving an AUC of roughly 0.81 and performing significantly better than random. In each of FIGS. 3A and 3B, the solid line corresponds to model performance while the dashed line corresponds to random performance on the holdout set.

It is clear that applying the invention before DDSP overwhelmingly improves the predictive accuracy of the patient models built in this example. This improvement over the state of the art allows prediction to become feasible, since without it, the resulting ML model, $F_N$, generalizes poorly and performs randomly on unseen data.

Computer-Based Implementations

In some examples, some or all of the processing described above can be carried out on a personal computing device, on one or more centralized computing devices, or via cloud-based processing by one or more servers. In some examples, some types of processing occur on one device and other types of processing occur on another device. In some examples, some or all of the data described above can be stored on a personal computing device, in data storage hosted on one or more centralized computing devices, or via cloud-based storage. In some examples, some data are stored in one location and other data are stored in another location. In some examples, quantum computing can be used. In some examples, functional programming languages can be used. In some examples, electrical memory, such as flash-based memory, can be used.

Figure 4:
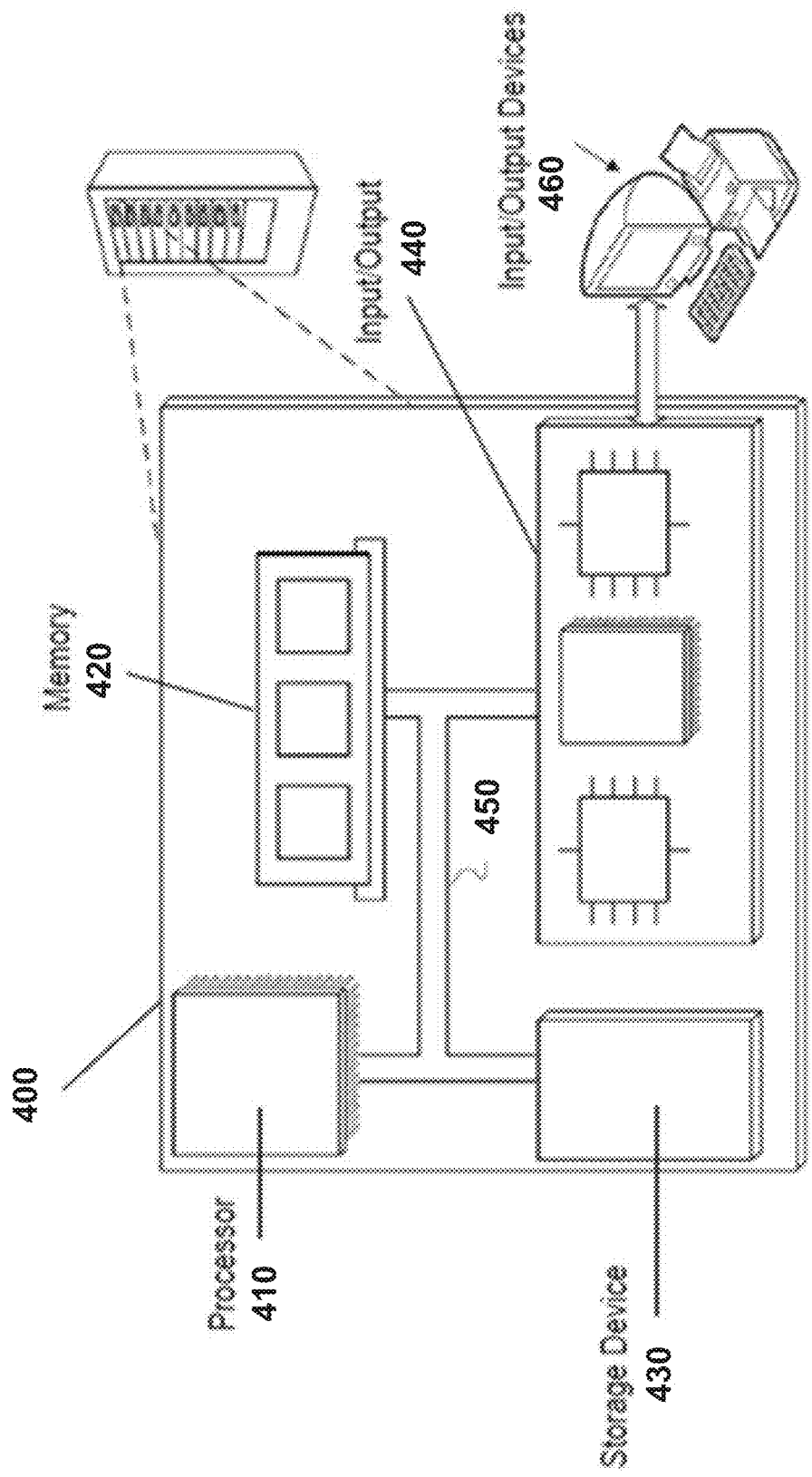
FIG. 4 depicts a block diagram of an example computer system.

FIG. 4 is a block diagram of an example computer system 400 that may be used in implementing the technology described in this document. General-purpose computers, network appliances, mobile devices, or other electronic systems may also include at least portions of the system 400. The system 400 includes a processor 410, a memory 420, a storage device 430, and an input/output device 440. Each of the components 410, 420, 430, and 440 may be interconnected, for example, using a system bus 450. The processor 410 is capable of processing instructions for execution within the system 400. In some implementations, the processor 410 is a single-threaded processor. In some implementations, the processor 410 is a multi-threaded processor. The processor 410 is capable of processing instructions stored in the memory 420 or on the storage device 430.

The memory 420 stores information within the system 400. In some implementations, the memory 420 is a non-transitory computer-readable medium. In some implementations, the memory 420 is a volatile memory unit. In some implementations, the memory 420 is a non-volatile memory unit.

The storage device 430 is capable of providing mass storage for the system 400. In some implementations, the storage device 430 is a non-transitory computer-readable medium. In various different implementations, the storage device 430 may include, for example, a hard disk device, an optical disk device, a solid-date drive, a flash drive, or some other large capacity storage device. For example, the storage device may store long-term data (e.g., database data, file system data, etc.). The input/output device 440 provides input/output operations for the system 400. In some implementations, the input/output device 440 may include one or more of a network interface devices, e.g., an Ethernet card, a serial communication device, e.g., an RS-232 port, and/or a wireless interface device, e.g., an 802.11 card, a 3G wireless modem, or a 4G wireless modem. In some implementations, the input/output device may include driver devices configured to receive input data and send output data to other input/output devices, e.g., keyboard, printer and display devices 460. In some examples, mobile computing devices, mobile communication devices, and other devices may be used.

In some implementations, at least a portion of the approaches described above may be realized by instructions that upon execution cause one or more processing devices to carry out the processes and functions described above. Such instructions may include, for example, interpreted instructions such as script instructions, or executable code, or other instructions stored in a non-transitory computer readable medium. The storage device 430 may be implemented in a distributed way over a network, such as a server farm or a set of widely distributed servers, or may be implemented in a single computing device.

Although an example processing system has been described in FIG. 4, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "system" may encompass all kinds of apparatus, devices, and machines for processing data, including by way of example a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

Terminology

The phraseology and terminology used herein is for the purpose of description and should not be regarded as limiting.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

The invention claimed is:

1. A method of improving quality of predictive model outputs, the method comprising:
receiving information describing a class association function that generates input data from source data, wherein the source data comprises a plurality of entities of one or more entity types, wherein the input data comprises a combination of the source data with class information such that entities in the input data are associated with one or more classes, and wherein the input data is configured to be input to a predictive model as data on which prediction is performed;
deriving, from the information describing the class association function, class association function characteristic data comprising inferences relating to operation of the class association function that are not derivable solely from the input data;
constructing a class-specific transformation function that transforms the input data into improved input data; and
transforming, using a computer processor, the input data into the improved input data using the class-specific transformation function and the class association function characteristic data, wherein the improved input data is configured to be input into the same predictive model as data on which prediction is performed, and wherein the improved input data is not based on output of the predictive model generated using the input data as input to the predictive model.

2. The method of claim 1, further comprising generating, using the computer processor, the input data by providing the source data as input to the class association function and receiving the input data as output from the class association function.

3. The method of claim 1, wherein the source data comprises data stored in computer memory, a database, data warehouse, data lake, data lakehouse, file system or object store.

4. The method of claim 1, wherein the information describing the class association function comprises a class association function that is directly introspectable.

5. The method of claim 1, wherein the information describing the class association function comprises a class association function that is not directly introspectable.

6. The method of claim 1, wherein the information describing the class association function is received from an external source.

7. The method of claim 1, wherein receiving the information describing the class association function comprises generating the information describing the class association function by approximating at least a portion of the class association function using information inferred from the source data and the class information.

8. The method of claim 1, wherein the deriving comprises one or more of:
(i) extracting entity-related information from the class association function;
(ii) applying the class association to one or more subsets of the input data to identify entity-level attributes; and
(iii) analyzing the information describing the class association function to determine an approximate implementation of the class association function.

9. The method of claim 1, wherein the information describing the class association function is incorporated into the class-specific transformation function, such that the class-specific transformation function generates the input data from the source data.

10. The method of claim 1, wherein the information describing the class association function information is either incorporated into the class-specific transformation function or used as in input to the class-specific transformation function.

11. The method of claim 1, further comprising providing the improved input data as input to the predictive model and predicting, using the predictive model, whether a particular entity will be assigned to a particular class.

12. The method of claim 1, wherein the improved input data, when used as input to the predictive model, results in the predictive model providing output of greater predictive accuracy compared to use of the input data as input to the predictive model.

13. A method of improving quality of predictive model outputs, the method comprising:
receiving class association function characteristic data derived from information describing a class association function that generates input data from source data, wherein the source data comprises a plurality of entities of one or more entity types, wherein the input data comprises a combination of the source data with class information such that entities in the input data are associated with one or more classes, wherein the input data is configured to be input to a predictive model as data on which prediction is performed, and wherein the class association function characteristic data comprises inferences relating to operation of the class association function that are not derivable solely from the input data;
constructing a class-specific transformation function that transforms the input data into improved input data; and
transforming, using a computer processor, the input data into the improved input data using the class-specific transformation function and the class association function characteristic data, wherein the improved input data is configured to be input into the same predictive model as data on which prediction is performed, and wherein the improved input data is not based on output of the predictive model generated using the input data as input to the predictive model.

14. A method of improving quality of predictive model outputs for a healthcare system, the method comprising:
receiving information describing a class association function that generates input data from source data, wherein the source data comprises healthcare information associated with a plurality of participants associated with a healthcare system, wherein the input data comprises a combination of the source data with class information such that participants associated with the healthcare system in the input data are associated with one or more classes, and wherein the input data is configured to be input to a predictive model as data on which prediction is performed;
deriving, from the information describing the class association function, class association function characteristic data comprising inferences relating to operation of the class association function that are not derivable solely from the input data;

constructing a class-specific transformation function that transforms the input data into improved input data;

transforming, using a computer processor, the input data into the improved input data using the class-specific transformation function and the class association function characteristic data, wherein the improved input data is configured to be input into the same predictive model as data on which prediction is performed, and wherein the improved input data is not based on output of the predictive model generated using the input data as input to the predictive model; and providing the improved input data as input to the predictive model and predicting, using the predictive model and the improved input data, whether a particular participant associated with the healthcare system will satisfy a healthcare-related condition.

15. The method of claim 14, wherein the predicting comprises predicting, using the predictive model, whether the particular participant associated with the healthcare system will satisfy a predicate over data associated with the particular participant.

16. The method of claim 15, wherein the predicate comprises a patient receiving a diagnosis, a patient receiving a procedure, a patient receiving a treatment, a healthcare professional making a diagnosis, a healthcare professional performing a procedure, a healthcare professional prescribing a treatment, a payer making a payment, a payer rejecting a claim, or any combination of the foregoing.

17. The method of claim 14, wherein deriving the class association function characteristic data comprises determining that entities are assigned to the one or more classes based on a first date associated with a first predicate over data associated with the entities.

18. The method of claim 17, wherein deriving the class association function characteristic data comprises determining that entities are assigned to the one or more classes based on a relation of (i) the first date associated with the first predicate to (ii) a second date associated with a second predicate over the data associated with the entities.

19. The method of claim 18, wherein transforming the input data into the improved input data comprises filtering the input data to remove information associated with at least one of (i) dates temporally following an earliest date of the second predicate and (ii) dates temporally preceding an earliest date of the second predicate.

20. The method of claim 14, wherein deriving the class association function characteristic data comprises determining that entities are assigned to the one or more classes based on an occurrence of a healthcare-related event comprising starting a therapy, receiving a treatment, receiving a procedure, or receiving a diagnosis.

21. The method of claim 20, wherein transforming the input data into the improved input data comprises filtering the input data to remove information associated with dates having a particular temporal relationship to a time or date associated with the healthcare-related event.

22. The method of claim 21, wherein the particular temporal relationship comprises an earlier time or data, a later time or date, or a same time or date.

23. The method of claim 14, wherein the participants associated with the healthcare system comprise at least one of patients, healthcare providers, healthcare-related organizations, and payers.

24. A system for improving quality of predictive model outputs, the system comprising:

a processor and a memory storing computer-executable instructions that, when executed by the processor, program the processor to perform the operation of transforming input data into improved input data using a class-specific transformation function and class association function characteristic data, wherein the improved input data is configured to be input into a predictive model as data on which prediction is performed, and wherein the improved input data is not based on output of the predictive model generated using the input data as input to the predictive model;

wherein the input data comprises a combination of source data with class information such that entities in the input data are associated with one or more classes, wherein the input data is configured to be input to the same predictive model as data on which prediction is performed, wherein the source data comprises a plurality of entities of one or more entity types;

wherein the class-specific transformation function is constructed to transform the input data into the improved input data; and wherein the class association function characteristic data is derived from information describing a class association function, wherein the class association function generates the input data from the source data, and wherein the class association function characteristic data comprises inferences relating to operation of the class association function that are not derivable solely from the input data.

25. The system of claim 24, wherein the processor further performs the operation of generating the input data by providing the source data as input to the class association function and receiving the input data as output from the class association function.

26. The system of claim 24, wherein the information describing the class association function comprises a class association function that is directly introspectable.

27. The system of claim 24, wherein the information describing the class association function comprises a class association function that is not directly introspectable.

28. The system of claim 24, wherein the information describing the class association function is generated by approximating at least a portion of the class association function using information inferred from the source data and the class information.

29. The system of claim 24, wherein the class association function characteristic data is derived by one or more of:

(i) extracting entity-related information from the class association function;

(ii) applying the class association to one or more subsets of the input data to identify entity-level attributes; and (iii) analyzing the information describing the class association function to determine an approximate implementation of the class association function.

30. The system of claim 24, wherein the processor further performs the operation of providing the improved input data as input to the predictive model and predicting, using the predictive model, whether a particular entity will be assigned to a particular class.

* * * * *